United States Patent
Yuyama et al.

(10) Patent No.: US 9,626,822 B2
(45) Date of Patent: Apr. 18, 2017

(54) MEDICINE SUPPLY DEVICE

(75) Inventors: Hiroyuki Yuyama, Osaka (JP);
Hirokazu Amano, Osaka (JP)

(73) Assignee: YUYAMA MFG. CO., LTD., Osaka (JP)

(*) Notice: Subject to any disclaimer, the term of this patent is extended or adjusted under 35 U.S.C. 154(b) by 4 days.

(21) Appl. No.: 13/638,201

(22) PCT Filed: Mar. 29, 2011

(86) PCT No.: PCT/JP2011/057810
§ 371 (c)(1),
(2), (4) Date: Sep. 28, 2012

(87) PCT Pub. No.: WO2011/125650
PCT Pub. Date: Oct. 13, 2011

(65) Prior Publication Data
US 2013/0026174 A1 Jan. 31, 2013

(30) Foreign Application Priority Data
Apr. 2, 2010 (JP) ................................. 2010-086275

(51) Int. Cl.
*B65D 83/00* (2006.01)
*G07F 11/00* (2006.01)
(Continued)

(52) U.S. Cl.
CPC .......... *G07F 11/00* (2013.01); *G07F 17/0092* (2013.01); *A61J 7/04* (2013.01); *G06F 19/3462* (2013.01)

(58) Field of Classification Search
CPC .................................... G07F 11/00; A61J 7/04
(Continued)

(56) References Cited

U.S. PATENT DOCUMENTS 7,040,077 B2 * 5/2006 Yasuoka et al. ................ 53/493
7,177,721 B2 * 2/2007 Kirsch et al. ................ 700/236
(Continued)

FOREIGN PATENT DOCUMENTS

| CN | 1511760 A | 7/2004 |
| CN | 101237845 A | 8/2008 |

(Continued)

OTHER PUBLICATIONS

An International Search Report, dated Jun. 7, 2011 in International Application No. PCT/JP2011/057810.
CN Office Action with English translation dated Oct. 8, 2013.

*Primary Examiner* — Michael K Collins
(74) *Attorney, Agent, or Firm* — Hauptman Ham, LLP

(57) ABSTRACT

A preparation task for medicine, which must be manually prepared in advance, is efficiently performed without error. A medicine supply device includes: a medicine supply means having a plurality of medicine receiving portions, the medicine supply means being configured to receive a medicine per a dosing time and appropriately discharge the received medicine; a display means including a plurality of display portions, the display portions being provided in association with the medicine receiving portions respectively; and a display control means configured to allow the display portion of the medicine receiving portion, which receives a corresponding medicine among the medicine receiving portions, to operate based on a prescription data. The display portion of the display means is configured to display a number corresponding to the dosing time of each medicine included in the prescription data.

2 Claims, 13 Drawing Sheets

(51) Int. Cl.
*G07F 17/00* (2006.01)
*G06F 19/00* (2011.01)
*A61J 7/04* (2006.01)

(58) Field of Classification Search
USPC .................................................. 221/89–91
See application file for complete search history.

(56) References Cited

U.S. PATENT DOCUMENTS

| | | | | |
|---|---|---|---|---|
| 7,258,249 | B1* | 8/2007 | Frederick | A61G 12/001 221/282 |
| 7,463,947 | B1* | 12/2008 | Frederick | G06F 19/327 700/231 |
| 7,689,316 | B1* | 3/2010 | Frederick | G06F 19/327 700/231 |
| 7,848,846 | B2 | 12/2010 | Uema et al. | |
| 7,861,495 | B2* | 1/2011 | Yuyama et al. | 53/246 |
| 7,873,435 | B2* | 1/2011 | Yuyama | G06Q 10/10 700/236 |
| 7,922,037 | B2* | 4/2011 | Ohmura | A61J 7/0084 221/123 |
| 8,209,943 | B2 | 7/2012 | Yuyama et al. | |
| 8,380,346 | B2* | 2/2013 | Chudy | G06F 19/3462 221/6 |
| 9,002,510 | B2* | 4/2015 | Chudy et al. | 700/242 |
| 2003/0074868 | A1* | 4/2003 | Yasuoka et al. | 53/493 |
| 2003/0230590 | A1* | 12/2003 | Gilmore | A61G 12/001 221/2 |
| 2004/0134043 | A1* | 7/2004 | Uema et al. | 24/297 |
| 2005/0209733 | A1* | 9/2005 | Gilmore | A61G 12/001 700/231 |
| 2009/0152291 | A1* | 6/2009 | Ohmura | A61J 7/0084 221/197 |
| 2009/0210247 | A1* | 8/2009 | Chudy | G06F 19/3462 705/2 |
| 2013/0126545 | A1* | 5/2013 | Chudy et al. | 221/1 |
| 2013/0158706 | A1* | 6/2013 | Chudy et al. | 700/242 |
| 2013/0218330 | A1* | 8/2013 | Chudy et al. | 700/244 |

FOREIGN PATENT DOCUMENTS

| | | |
|---|---|---|
| CN | 101568470 A | 10/2009 |
| JP | 2509821 B2 | 4/1996 |
| JP | 8-183502 A | 7/1996 |
| JP | 2866543 B2 | 12/1998 |
| JP | 2004-203433 A | 7/2004 |
| JP | 2007-297066 A | 11/2007 |
| JP | 4253357 B1 | 4/2009 |

* cited by examiner

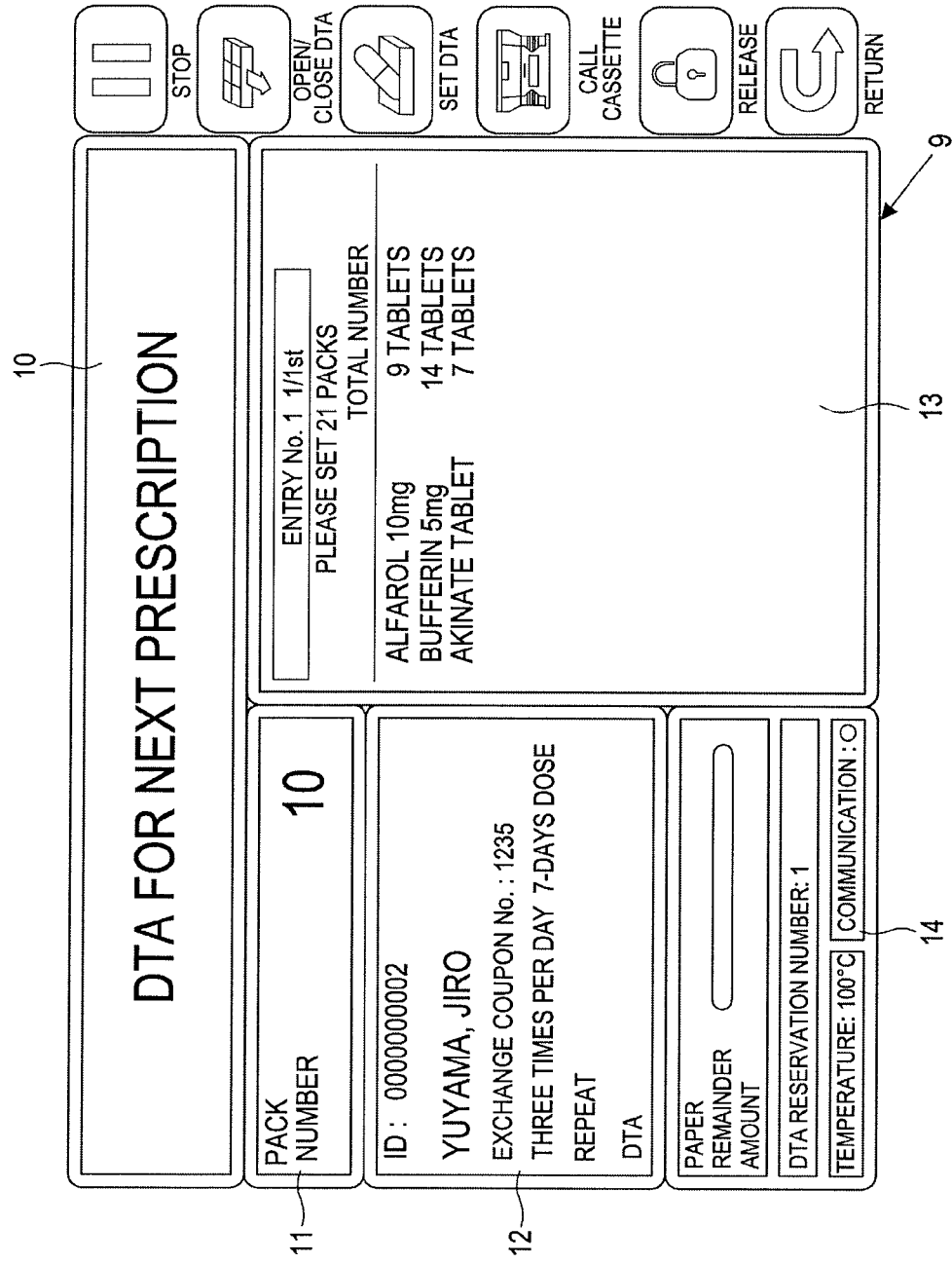

FIG. 3B

PATIENT'S NAME : YUYAMA, TARO
THREE TIMES PER DAY  7-DAYS DOSE  REPEAT

① MEDICINE NAME: ALFAROL 10mg          9 TABLETS

|  | 1st DAY | 2nd DAY | 3rd DAY | 4th DAY | 5th DAY | 6th DAY | 7th DAY |
|---|---|---|---|---|---|---|---|
| MORNING | 1 |  |  |  |  |  |  |
| AFTERNOON |  | 1 | 1 | 1 | 1 | 1 | 1 |
| EVENING |  |  |  |  |  | 1 | 1 |

② MEDICINE NAME: BUFFERIN 5mg          14 TABLETS

|  | 1st DAY | 2nd DAY | 3rd DAY | 4th DAY | 5th DAY | 6th DAY | 7th DAY |
|---|---|---|---|---|---|---|---|
| MORNING | 1 | 1 | 1 | 1 | 1 | 1 | 1 |
| AFTERNOON |  |  |  |  |  |  |  |
| EVENING | 1 | 1 | 1 | 1 | 1 | 1 | 1 |

③ MEDICINE NAME: AKINATE TABLET         7 TABLETS

|  | 1st DAY | 2nd DAY | 3rd DAY | 4th DAY | 5th DAY | 6th DAY | 7th DAY |
|---|---|---|---|---|---|---|---|
| MORNING |  |  |  |  |  |  |  |
| AFTERNOON | 1 | 1 | 1 | 1 | 1 | 1 | 1 |
| EVENING |  |  |  |  |  |  |  |

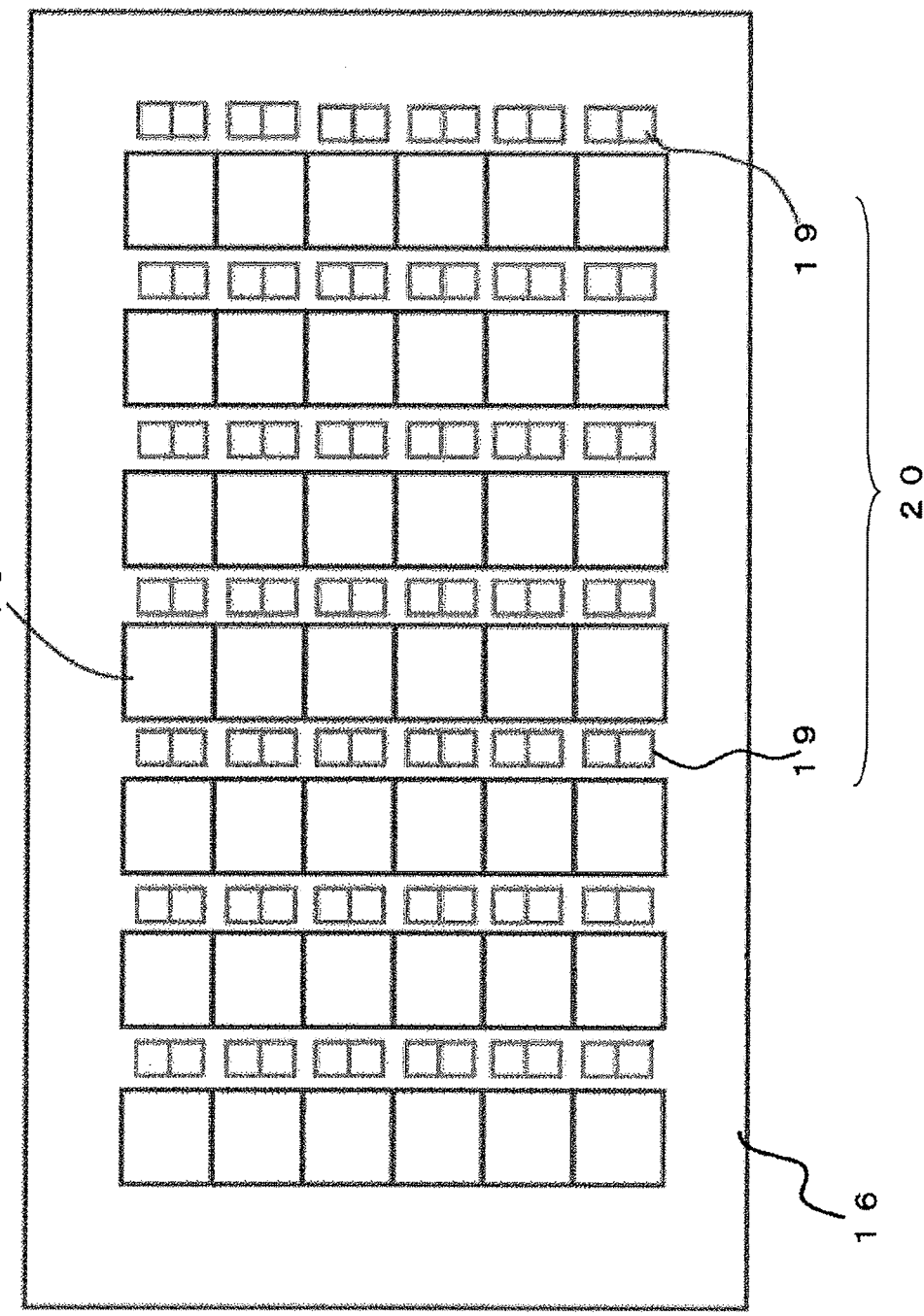

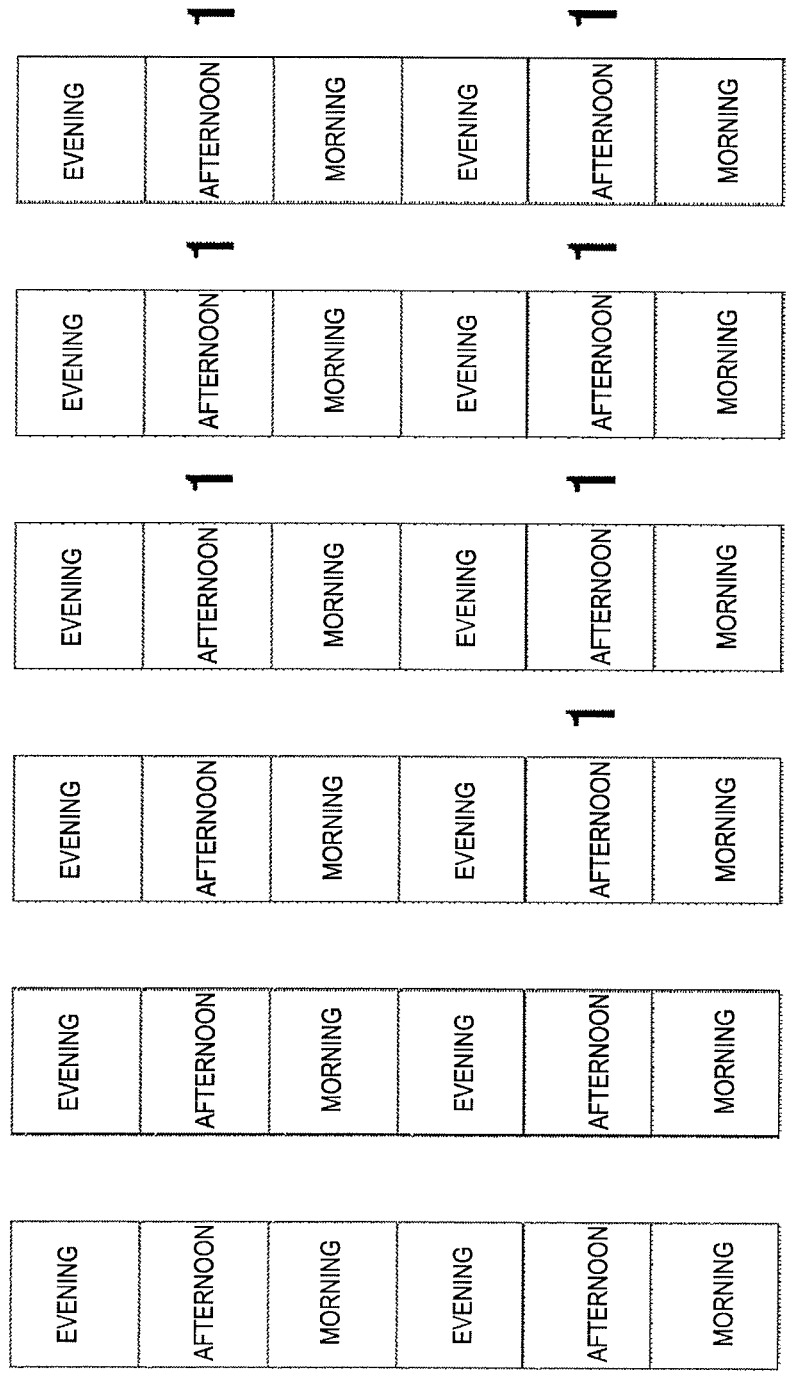

FIG. 7

DTA FOR NEXT PRESCRIPTION

PACK NUMBER: 10

ID: 00000000002
YUYAMA, JIRO
EXCHANGE COUPON No.: 1235
THREE TIMES PER DAY 7-DAYS DOSE
REPEAT
DTA

ENTRY No. 1  1/1st
PLEASE SET 21 PACKS
SE

| | |
|---|---|
| ALFAROL 10mg | 2 TABLETS ○ |
| BUFFERIN 5mg | 1 TABLETS ◉ |
| AKINATE TABLET | 1 TABLETS ● |

PAPER REMAINDER AMOUNT
DTA RESERVATION NUMBER: 1
TEMPERATURE: 100°C   COMMUNICATION: ○

Buttons: STOP, OPEN/CLOSE DTA, SET DTA, CALL CASSETTE, RELEASE, RETURN

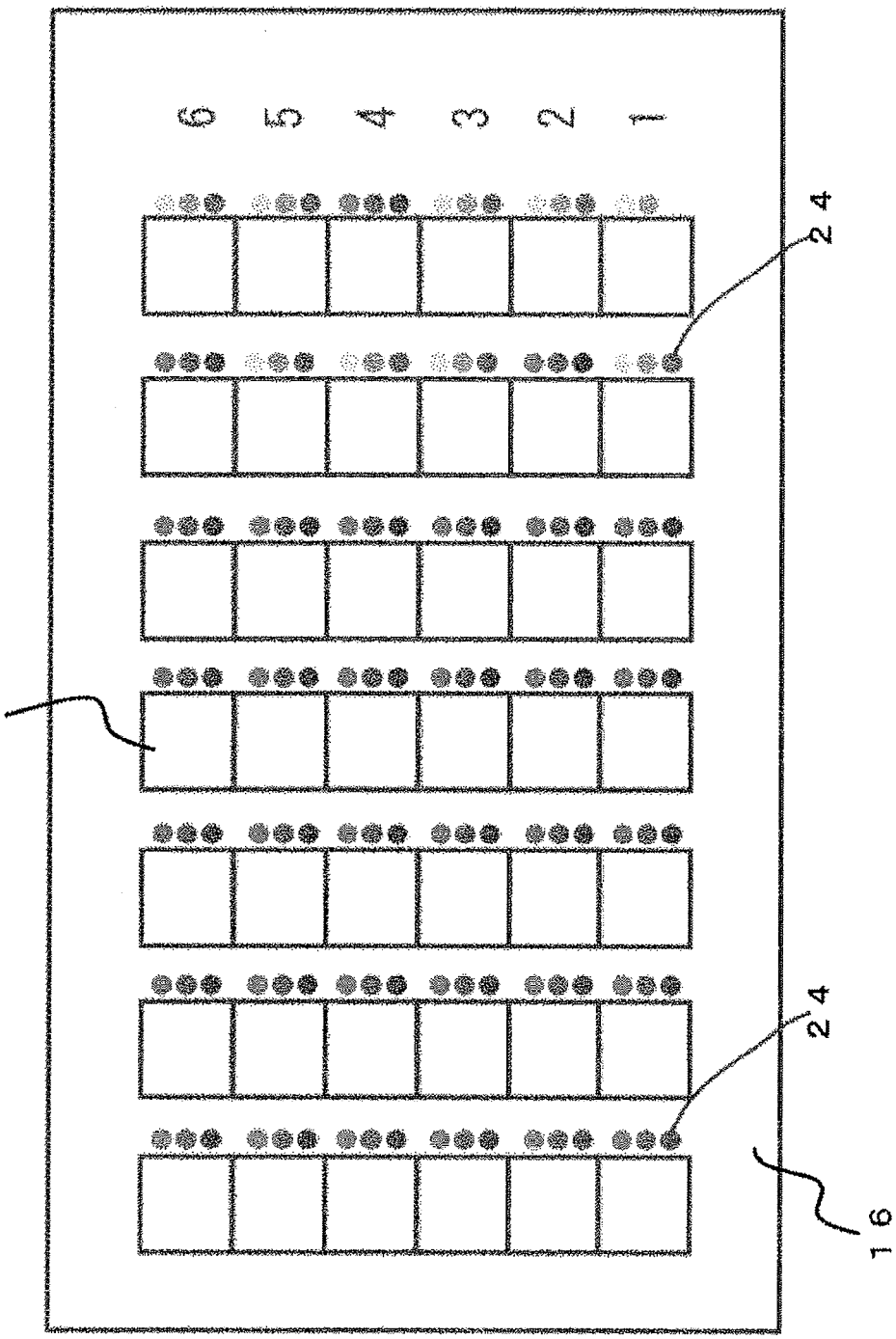

MEDICINE SUPPLY DEVICE

RELATED APPLICATIONS

The present application is a National Phase of PCT/JP2011/057810, filed Mar. 29, 2011 and claims priority from, Japanese Application No. 2010-086275, filed Apr. 2, 2010.

TECHNICAL FIELD

The present invention relates to a medicine supply device.

BACKGROUND

There exists in the art a medicine supply device that is configured to indicate a receiving compartment, to which a medicine is to be placed, by turning on a guide means provided in association with the receiving compartments respectively based on a prescription data, and to allow a display means provided separately from the guide means to display the quantity of one dose of the medicine (see, e.g., Patent Document 1).

In the aforementioned Patent Document 1, the guide means provided at the receiving compartment indicates where the receiving compartment for receiving the medicine locates. However, as for the quantity of the medicine to be placed, there is a need to confirm the displayed contents of the display means provided separately. Thus, this requires the user to shift his eyes extensively, which leads to errors in the quantity of the medicine to be placed.

Further, there exists in the art another medicine supply device wherein a plurality of compartments are formed lengthwise and breadthwise in a preliminary distribution cassette and a display means is provided for indicating the position or range of the compartments to be used according to the content of a prescription for manual distribution (see, e.g., Patent Document 2). There exists in the art yet another medicine supply device including a means for displaying the number of measures used in a preliminary distribution cassette (see, e.g., Patent Document 3).

In the aforementioned Patent Documents 2 and 3, only the number of the measures used in the preliminary distribution cassette is displayed, thus indicating the number of the measures, to which medicine is manually distributed. However, it is uncertain which and how much medicine is to be manually distributed to which measures. That is, efficient performance of a manual distribution task for the medicines cannot be expected.

Patent Document 1: Japanese Laid-Open Patent Application No. 2004-203433
Patent Document 2: Japanese Patent Publication No. 2509821
Patent Document 3: Japanese Patent Publication No. 2866543

SUMMARY

It is an object of the present invention to provide a medicine supply device, which is capable of performing a manual distribution task for medicines, which must be manually prepared in advance, efficiently and without error.

As measures for achieving the foregoing object, the present invention provides a medicine supply device including: a medicine supply means having a plurality of medicine receiving portions, the medicine supply means being configured to receive a medicine per a dosing time and appropriately discharge the received medicine; a display means including a plurality of display portions, the display portions being provided in association with the medicine receiving portions respectively; and a display control means configured to allow the display portion of the medicine receiving portion, which receives a corresponding medicine among the medicine receiving portions, to operate based on a prescription data. The display portion of the display means is configured to display a number corresponding to the dosing time of each medicine included in the prescription data.

According to such configuration, when medicine is placed in each medicine receiving portion, it can be indicated to the user through the display portion provided in the medicine supply means how much medicine must be placed into which medicine receiving portion. Thus, the user may put the corresponding medicine to the medicine receiving portion, which is identified by the display portion, by the indicated quantity, in a state where the medicine receiving portion and the display portion are located in the same visual field. Thus, the user can efficiently proceed with the task without error.

As measures for achieving the foregoing object, the present invention provides a medicine supply device including: a medicine supply means having a plurality of medicine receiving portions, the medicine supply means being configured to randomly receive medicine and appropriately discharge the received medicine; a display means including a plurality of display portions, the display portions being provided in association with the medicine receiving portions respectively; and a display control means configured to allow the display portion of the medicine receiving portion, to which a corresponding medicine is placed among the medicine receiving portions, to operate based on a prescription data. The display means further includes a second display portion configured to display a prescribed number of the corresponding medicine included in the prescription data.

According to such configuration, it can be determined through the indication portions provided in the medicine supply means which medicine receiving portion must receive the medicine. Further, it can be determined through the second display portion provided in the medicine supply means how much medicine must be put. The expensive second indication portion for displaying the quantity is provided separately from the display portions provided in association with the respective medicine receiving portions. Thus, a decrease in the number of the second indication portion can reduce manufacturing costs.

As measures for achieving the foregoing object, the present invention provides a medicine supply device including: a medicine supply means having a plurality of medicine receiving portions, the medicine supply means being configured to randomly receive a medicine and appropriately discharge the received medicine; a display means including a plurality of display portions, the display portions being provided in association with the medicine receiving portions respectively; and a display control means configured to allow the display portion of the medicine receiving portion, to which a corresponding medicine is placed among the medicine receiving portions, to operate based on a prescription data. The plurality of the display portions of the display means are configured to be distinguishable. When the prescription data includes a plurality of types of medicine, the display control means allows the display portions to operate in association with each type of medicine.

According to such configuration, even in the case where the prescription data includes a plurality of types of medicines, it can be determined at a glance which medicine receiving portion receives which medicine. Thus, a plurality of types of medicine can be efficiently placed into the medicine receiving portions simultaneously.

Preferably, the medicine supply device further includes a second display means configured to display at least a medicine name among the prescription data. When the prescription data includes a plurality of types of medicines, the display control means allows the second display means to distinguishably display the medicines and allows the display portions of the display means provided in the medicine supply means to distinguishably operate in association with a display made by the second display means.

According to such configuration, the display portions of the medicine supply means and the display means are distinguishably operated in association with the medicine names displayed by the second display portion. Thus, the task can be performed more efficiently.

According to the present invention, the display portions, which are provided in association with the respective medicine receiving portions of the medicine supply means, are configured to display the quantity of the medicines, which are placed into each medicine receiving portion. Thus, without shifting his eyes, the user can determine how much medicine is placed into which medicine supply portions. Accordingly, the user can proceed with the task more efficiently without errors in the receipt positions and the received numbers of the medicines.

BRIEF DESCRIPTION OF THE DRAWINGS

FIG. 3A illustrates a guide screen displayed on an operation panel shown in FIG. 1.

FIG. 3B is a diagram showing detailed dosing time and dosage of an example shown in FIG. 3A.

FIG. 4A is a top view schematically showing a medicine manual-distribution supply section shown in FIG. 1.

FIG. 4D illustrates a display form of the 7-segment displays in the medicine manual-distribution supply section when continuously packaging ARKINATE TABLET shown in FIG. 3A.

FIG. 7 illustrates a guide screen displayed in the operation panel in accordance with another embodiment.

FIG. 8 is a top view schematically showing a medicine manual-distribution supply device according to another embodiment.

DETAILED DESCRIPTION

Hereinafter, descriptions will be made as to embodiments of the present invention with reference to the accompanying drawings. The descriptions below are only for purposes of illustration and are not intended to limit the present invention, applications thereof or use thereof.

Figure 1:
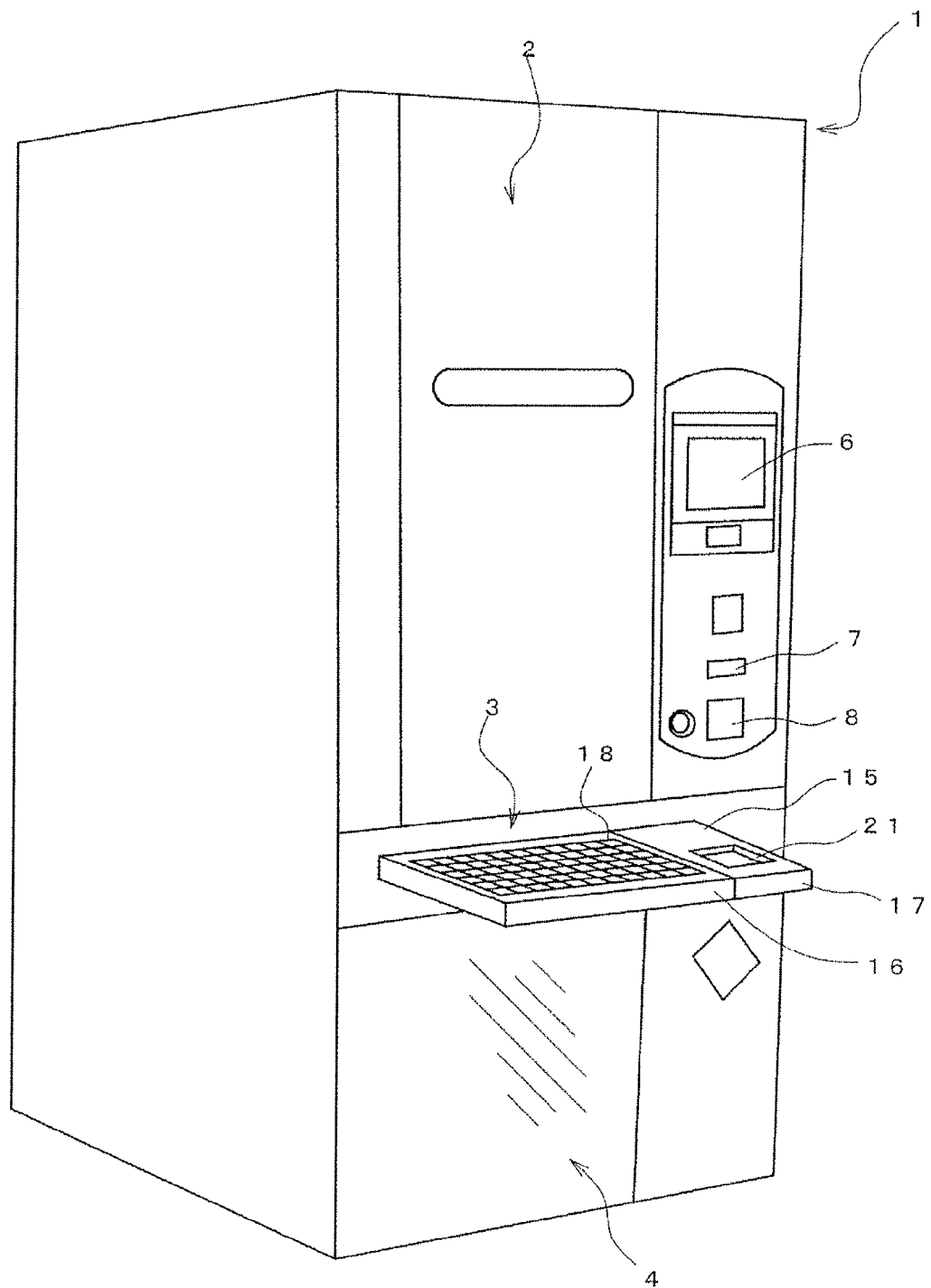
FIG. 1 is a perspective view schematically showing a medicine packaging apparatus including a medicine supply device according to an embodiment.

FIG. 1 shows a medicine packaging apparatus according to an embodiment. The medicine packaging apparatus generally includes, in an apparatus body 1, an automatic medicine supply device 2, a manual medicine supply device 3 (manual distribution device=DTA device), a medicine packaging device 4 and a control device 5.

The apparatus body 1 has a shape of an approximately rectangular parallelepiped. In the right of an upper half of a front of the apparatus body shown in FIG. 1, an operation panel 6, a barcode reader 7 and a journal printer 8 are arranged sequentially from above. The operation panel 6 comprises a touch panel and is configured to display, for example, a guide screen 9.

As shown in FIG. 3, the guide screen 9 includes a title section 10, a pack number section 11, a patient section 12, a prescription details section 13, an others section 14 and various buttons. The title section 10 displays what the displayed contents relate to. In the example shown in FIG. 3, "DTA FOR NEXT PRESCRIPTION" is displayed in the title section 10, thus informing the user that the displayed contents are that the next prescription relates to medicines to be dispensed from the manual medicine supply device 3. The pack number section 11 displays a total packaging number of a particular prescription. The patient section 12 displays a patient's name, a usage instruction (a dosing method of a medicine), etc. The prescription details section 13 displays the name of the medicine to be prescribed, the dosage amount, etc. The others section 14 includes a paper remainder amount (the remainder amount of a packaging paper), a DTA reservation number (the number of prescriptions set to the manual medicine supply device 3), temperature (the sealing temperature of the packaging paper) and communication (the communication status to a server, O is displayed under communication and if otherwise, X is displayed). The barcode reader 7 is used to read a barcode of a label adhered to a cassette (this will be described later) and to read medicine information. The journal printer 8 is for printing a prescription data (e.g., the patient's name, the name of a medicine, the usage instructions, the dosage, etc.)

For example, the automatic medicine supply device 2 may have the same configuration as that of the prior art (e.g., see Japanese Laid-Open Patent Application No. Hei 8-183502). That is, a plurality of medicine cassettes, each of which receives the same type of medicine (this mainly includes tablet medicines and also includes capsule medicines), are provided in the automatic medicine supply device. Further, the automatic medicine supply device is configured to automatically dispense the medicine in a number consistent with the prescription quantity from the medicine cassette receiving the corresponding medicine, based on the prescription data. Further, the automatic medicine supply device is configured to supply the medicine to the medicine packaging device 4 (this will be described below) such that they can be packaged one pack at a time.

The manual medicine supply device 3 includes a slide table 15 that is provided to be drawn out in a forward direction from a front central portion (slightly lower portion of the central portion) of the apparatus body 1. The slide table 15 includes a manual medicine supply section 16 and a cassette placing section 17.

The manual medicine supply section 16 is compartmentalized into a lattice shape to thus define a plurality of medicine receiving portions 18. The medicine for one dose (the medicine per a dosing time), which is to be packaged by the medicine packaging device 4 as described below, is manually placed into each medicine receiving portion 18 from medicine bottles (not shown). A bottom of each medicine receiving portion 18 is configured to be opened. The bottoms are opened in sequence when the slide table 15 is received in the apparatus body 1, thereby discharging the medicine received therein to the medicine packaging device 4. A 7-segment display 19, which comprises light emitting diodes (LEDs), is disposed adjacent to each medicine receiving portion 18 (in this embodiment, on the right side of the medicine receiving portion), thus constituting a display member 20 (see FIG. 4).

Further, instead of the LEDs, a display of an irradiation type, or a flat display such as a liquid-crystal panel, an organic electroluminescence panel, etc. can be used as the display member 20. In particular, in the case of employing a touch panel, the touch panel may be configured to change its background color through touch-manipulation on its portion corresponding to the measure, at which the manual distribution is completed, thus allowing the user to be aware of the completion status of each measure at a glance. Further, in this case, an alarm may be emitted through a systematic check on whether there is any omission when the task is finished. Further, the position of the display member 20 should not be limited to the right side of the medicine receiving portion 18. The display member may be provided in any position such as the left side, the upper side, the lower side, etc. as long as the correspondence relationship to the medicine receiving portion 18 can be identified.

The cassette placing section 17 includes a recess 21, which is rectangular in a top view, such that the cassette (the tablet cassette, the medicine bottle, etc.) to be placed thereon cannot be out of position. The cassette (medicine container) (not shown) to be placed on the recess 21 is provided with an RFID (Radio Frequency Identification). Information stored in the RFID is read through an RFID reader 22 (see FIG. 2) provided in the cassette placing section 17.

For example, the medicine packaging device 4 may have the same configuration as that of the prior art (e.g., see Japanese Laid-Open Patent Application No. Hei 8-183502). That is, the medicine supplied from the automatic medicine supply device 2 or the manual medicine supply device 3 is collected through a hopper (not shown). The collected medicine is fed to a bifold package paper, which is folded in an obliquely downward longitudinal direction. The packaging paper is sealed at predetermined pitches and thus the supplied medicine is packaged one pack at a time. The usage instructions, the dosage, etc. are appropriately printed on the package paper before sealing the packaging paper.

Figure 2:
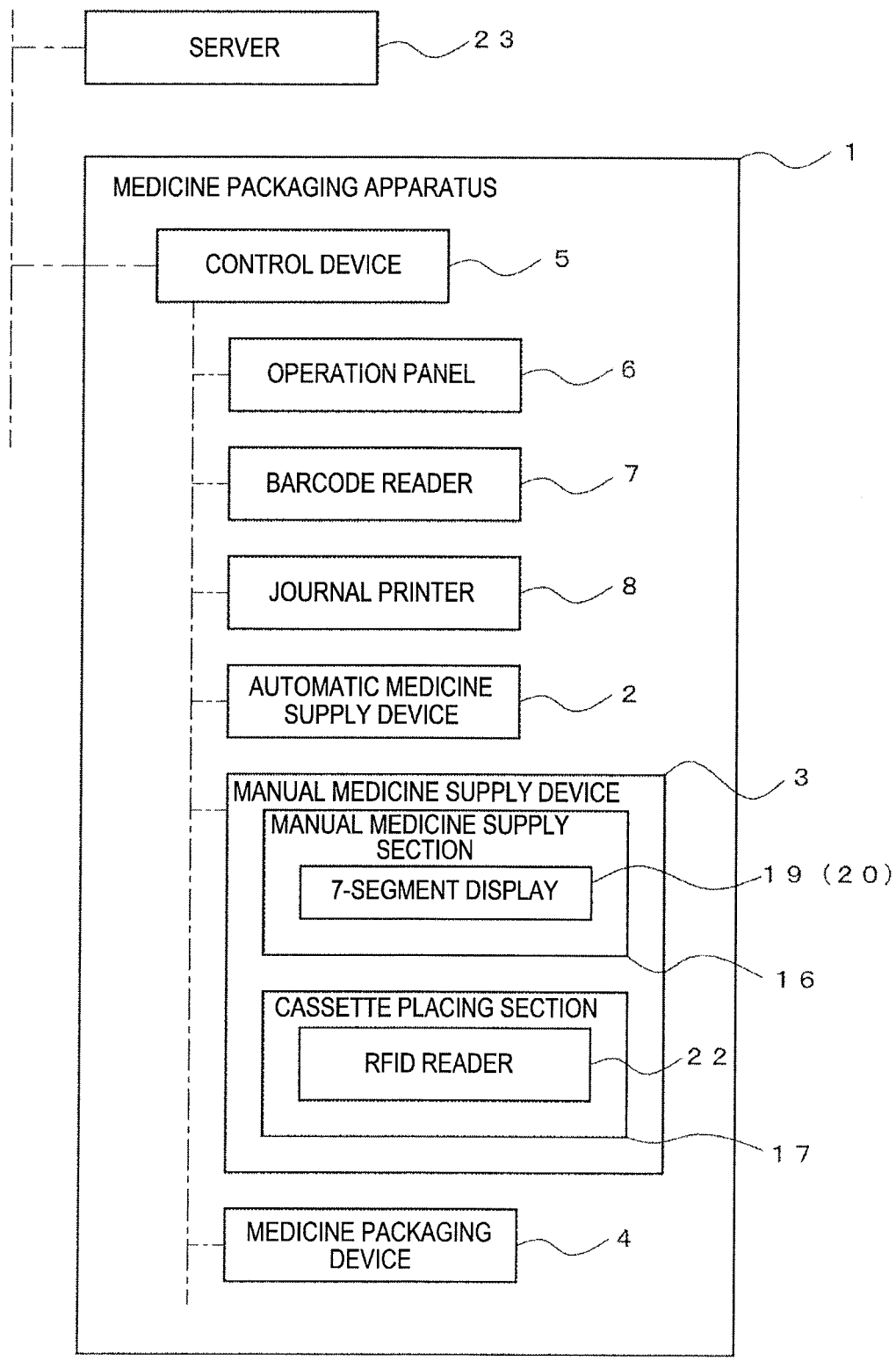
FIG. 2 is a block diagram of the medicine packaging apparatus according to an embodiment.

As shown in FIG. 2, the control device 5 performs a dispensing control of dispensing the corresponding medicine from the automatic medicine supply device 2 or the manual medicine supply device 3, based on the prescription data inputted from a server 23 (host computer) or a keyboard (not shown). Further, if the RFID of the cassette is read through the RFID reader or the barcode printed on the adhered label is read through the barcode reader 7, then the control device ascertains whether the medicine according to such read accords with the medicine included in the prescription data. Further, as described below, the control device performs a display control of allowing the operation panel 6 to display the name of the medicine or turning on the display member 20 of the manual medicine supply device 3 so as to display the quantity. Further, the control device allows the journal printer 8 to print the predetermined items. Furthermore, the control device allows the medicine packaging device 4 to package the medicine supplied from the automatic medicine supply device 2 or the manual medicine supply device 3 one pack at a time.

Figure 5:
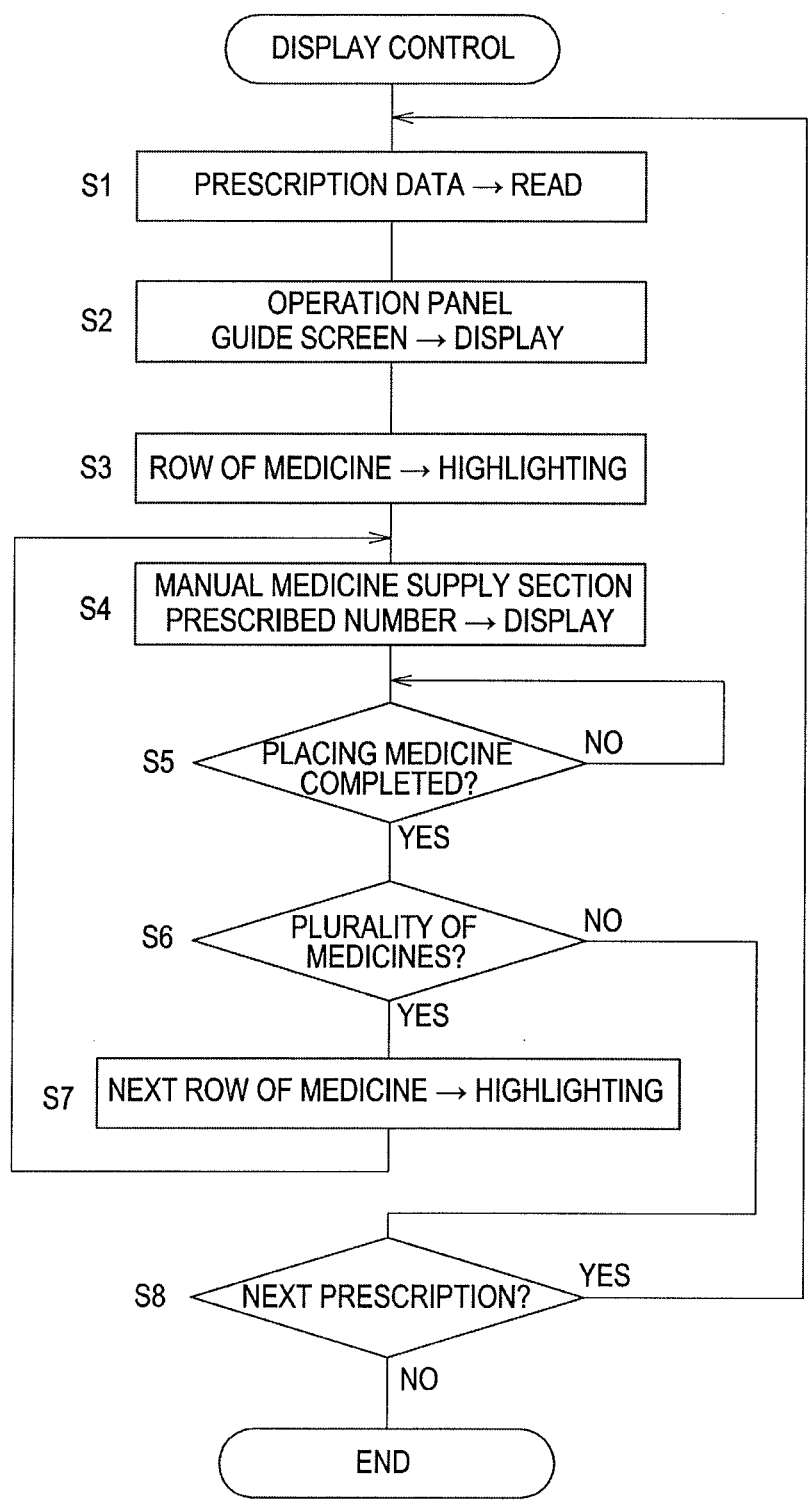
FIG. 5 is a flow chart showing a display control process performed by a control device shown in FIG. 2.

Next, descriptions are made as to the operation of the above-configured medicine packaging apparatus along the flow chart shown in FIG. 5.

First, the prescription data is read in (Step S1) and the guide screen 9 shown in FIG. 3 is displayed on the operation panel 6 of the apparatus body 1 (Step S2). The list of the name and dosage of the medicine to be supplied to the manual medicine supply device 3 is displayed on the prescription details section 13. When the medicine to be put to the medicine receiving portion 18 or the row of such a medicine is selected from the list, it is highlighted through highlighting display, reversing display, etc. (Step S3). Further, it is preferred that the barcode on a medicine bottle (or the RFID) is read in when the medicine is selected from the list displayed on the prescription details section 13. This eliminates wrong selection of a target medicine. In particular, even in the case where the prescriptions for many patients are dealt with all together through the DTA and the prescriptions include the same type of medicine (in this case, there is a plurality of the patient name sections. More details related thereto may be found in Japanese Patent No. 4253357), wrong selection can be avoided, thus enhancing the workability of manual distribution.

Figure 4B:
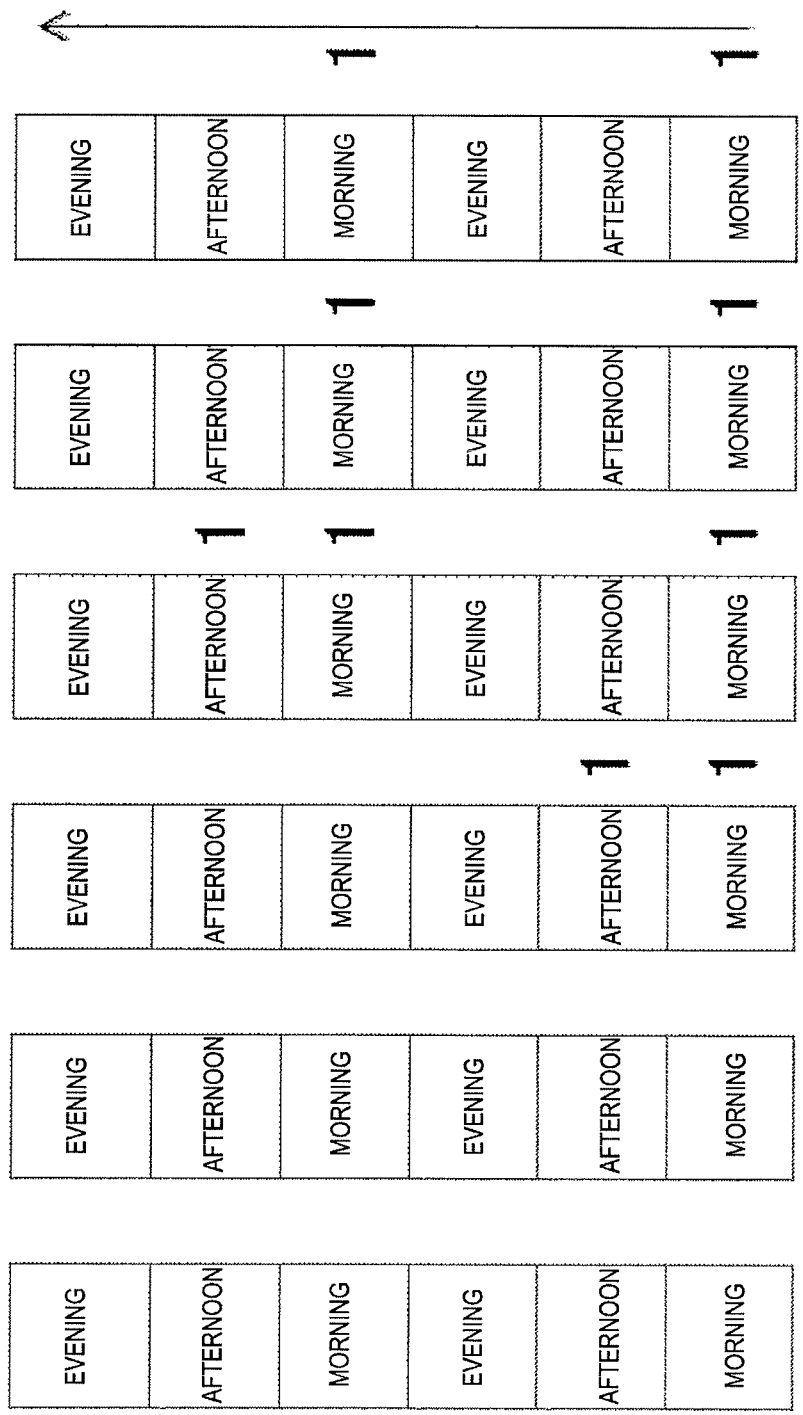
FIG. 4B illustrates a display form of 7-segment displays in the medicine manual-distribution supply section when continuously packaging ALFAROL shown in FIG. 3A.
Figure 4C:
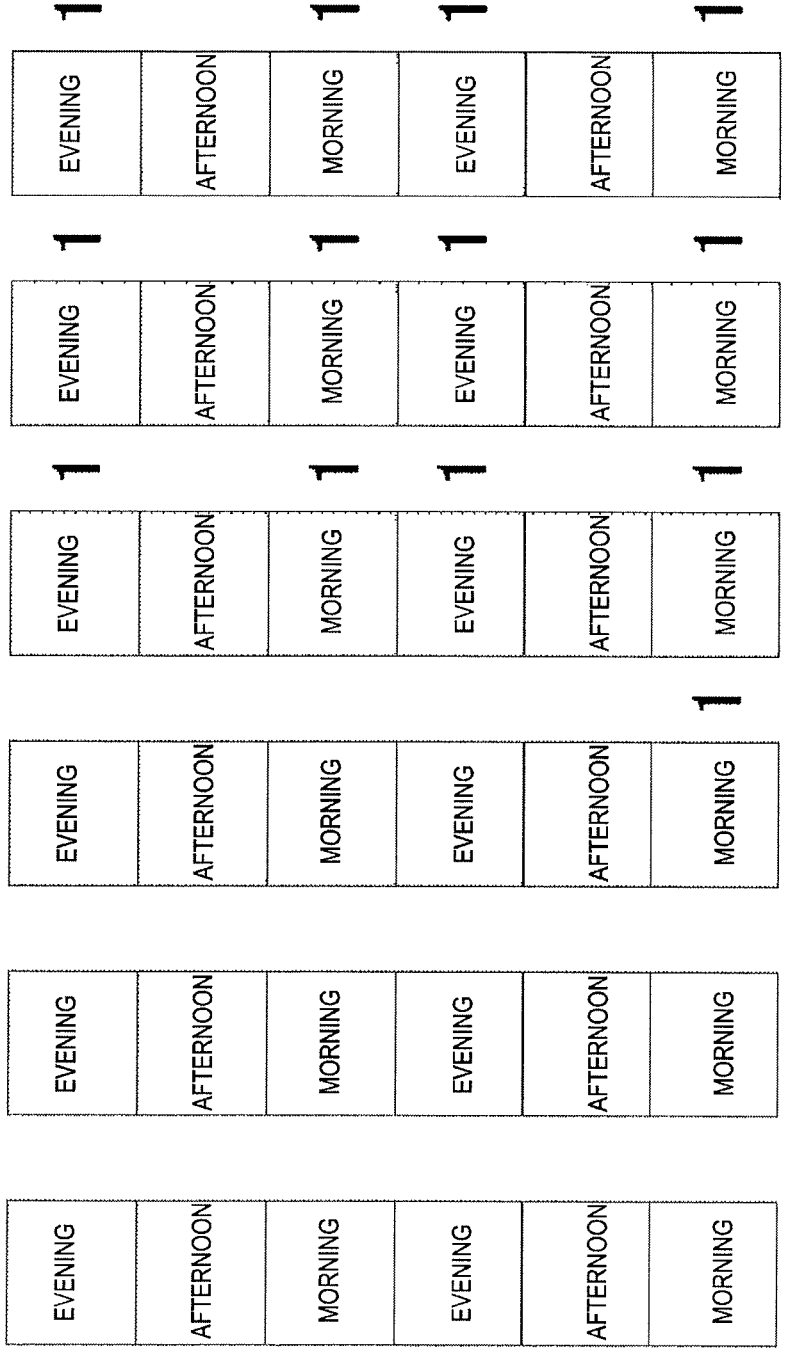
FIG. 4C illustrates a display form of the 7-segment displays in the medicine manual-distribution supply section when continuously packaging BUFFERIN shown in FIG. 3A.
Figure 4E:
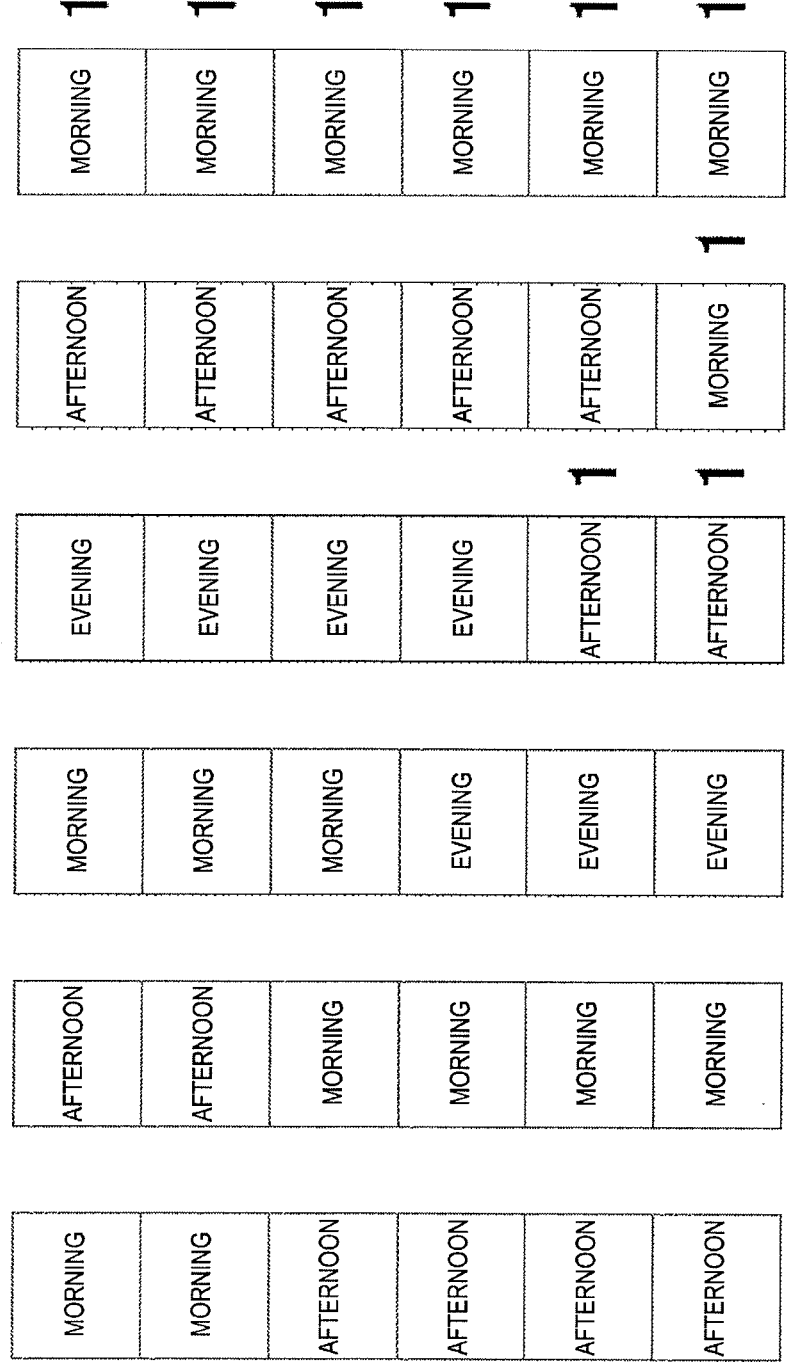
FIG. 4E illustrates a display form of the 7-segment displays in the medicine manual-distribution supply section when repeatedly packaging ALFAROL shown in FIG. 3A.

Further, in the manual medicine supply section 16, the display member 20, which corresponds to the medicine receiving portion 18, which must receive the medicine distinguishably displayed in the operation panel 6, displays the prescribed number (Step S4). Specifically, according to the example illustrated in FIG. 3A (ALFAROL 10 mg nine tablets, BUFFERIN 5 mg fourteen tablets, AKINATE TABLET seven tablets), the 7-segment displays 19 of the display member 20 shown in FIG. 4A make the following display. That is, the detailed dosing time and quantity of the example illustrated in FIG. 3A are as shown in FIG. 3B. The example of ALFAROL has nine tablets in sum, which have a seven-day dose of one tablet per day (morning dosing time) and a two-day dose of one tablet per day (6th day afternoon and a 7th day afternoon dosing time). Further, the example of BUFFERIN has fourteen tablets in sum, which have a seven-day dose of one tablet per day (morning dosing time) and a seven-day dose of one tablet per day (evening dosing time). Further, the example of AKINATE TABLET has seven tablets in sum, which have a seven-day dose of one tablet per day (afternoon dosing time). In the case of continuously packaging (an example of packaging medicine in accordance with a dosing order of morning—afternoon—evening— . . . ), as for the ALFAROL, "1" is displayed by the 7-segment displays 19, which correspond to a 1st day morning (located at a lower right corner) to a 7th day morning, respectively, and the 7-segment displays 19, which correspond to a 6th day morning and a 7th day morning, as shown in FIG. 4B. Similarly, the example of BUFFERIN is as shown in FIG. 4C and the example of AKINATE TABLET is as shown in FIG. 4D. Further, in the case of repeatedly packaging (an example of packaging medicines in accordance with dosing time such as morning—morning—afternoon—afternoon— . . . ), the example of ALFAROL is as shown in FIG. 4E.

The user may look at the prescription details section 13 of the display panel and confirm the medicine to be prescribed. Then, the user may remove the cassette (not shown) from a medicine shelf (not shown) and then, in accordance with the number which the display member 20 turned on in the manual medicine supply section 16 displays, place the medicine in an amount consistent with the displayed number to the corresponding medicine receiving portion 18 from the cassette.

Once starting the task, the user may place the predetermined number of medicine to each of the medicine receiving portions 18 in accordance with the display made by the display member 20. Thus, the user does not need to shift his eyes to the display panel in order to confirm the medicine receiving portion every time when the medicine receiving portion 18 for receiving the medicine changes. Accordingly, the corresponding medicine can be efficiently placed into each medicine receiving portion 18 without mistake. Further, when the user finishes the task of manually distributing the corresponding medicine to each medicine receiving portion 18, the user may manipulate a DTA set button of the operation panel 6.

If the DTA set button is manipulated and it is detected that the manual distribution task is completed (Step S5), then it is decided whether a plurality of the medicine names are displayed in the prescription details section 13 of the operation panel 6 (Step S6). If there is a plurality of the medicine names, then the medicine next displayed in the prescription details section 13 is highlighted such that it can be distinguished from others (Step S7). Subsequently, the display control process returns to said Step S4 and the same processes are performed. Accordingly, even in the case where the prescription data includes a plurality of medicine, the user can determine, at a glance, which medicine must be placed into the medicine receiving portion 18 at present. Similar to the forgoing, the user may look at the prescription details section 13 and confirm the medicine to be prescribed. Then, the user may remove the cassette from the medicine shelf (not shown) and then, in accordance with the display made by the display member 20 of the manual medicine supply section 16, place the medicine into the corresponding medicine receiving portion 18.

Next, if the processes for all the medicine included in any prescription data, which are displayed on the operation panel 6, are completed, then it is decided whether there is a next prescription data (Step S8). If there is no next prescription data, then the process is ended. If there is a next prescription data, the display control process returns to Step S1 and the above-described processes are repeated for the next prescription data. Further, in the case of shifting the distinguishable display to the next medicine in the operation panel 6, a sensor for detecting medicine may be provided in the medicine receiving portion 18 and said shift may be automatically performed by confirming that the medicine receiving portion receives the medicine.

As described above, according to the medicine supply device of the foregoing embodiment, the display members 20 are provided in association with the respective medicine receiving portions 18, thus indicating the following matters: which medicine receiving portion 18 must receive the medicine included in the prescription data; and how much medicine must be received. Accordingly, the user can proceed with the task without confirming the display of the operation panel in each case. Thus, the medicine supply device is very efficient. Further, since the above matters are displayed next to the medicine receiving portion 18 for receiving the medicine, the user does not make a mistake in how much medicine is placed. Further, an examination task after the completion of the manual distribution task for medicine can be efficiently performed.

The present invention should not be limited to the configuration of the foregoing embodiment. Various modifications may be made.

For example, in the foregoing embodiment, the manual medicine supply section 16 is configured such that the 7-segment displays 19 are disposed so as to correspond to the respective medicine receiving portions 18. The manual medicine supply section 16 may be configured as follows.

Figure 6:
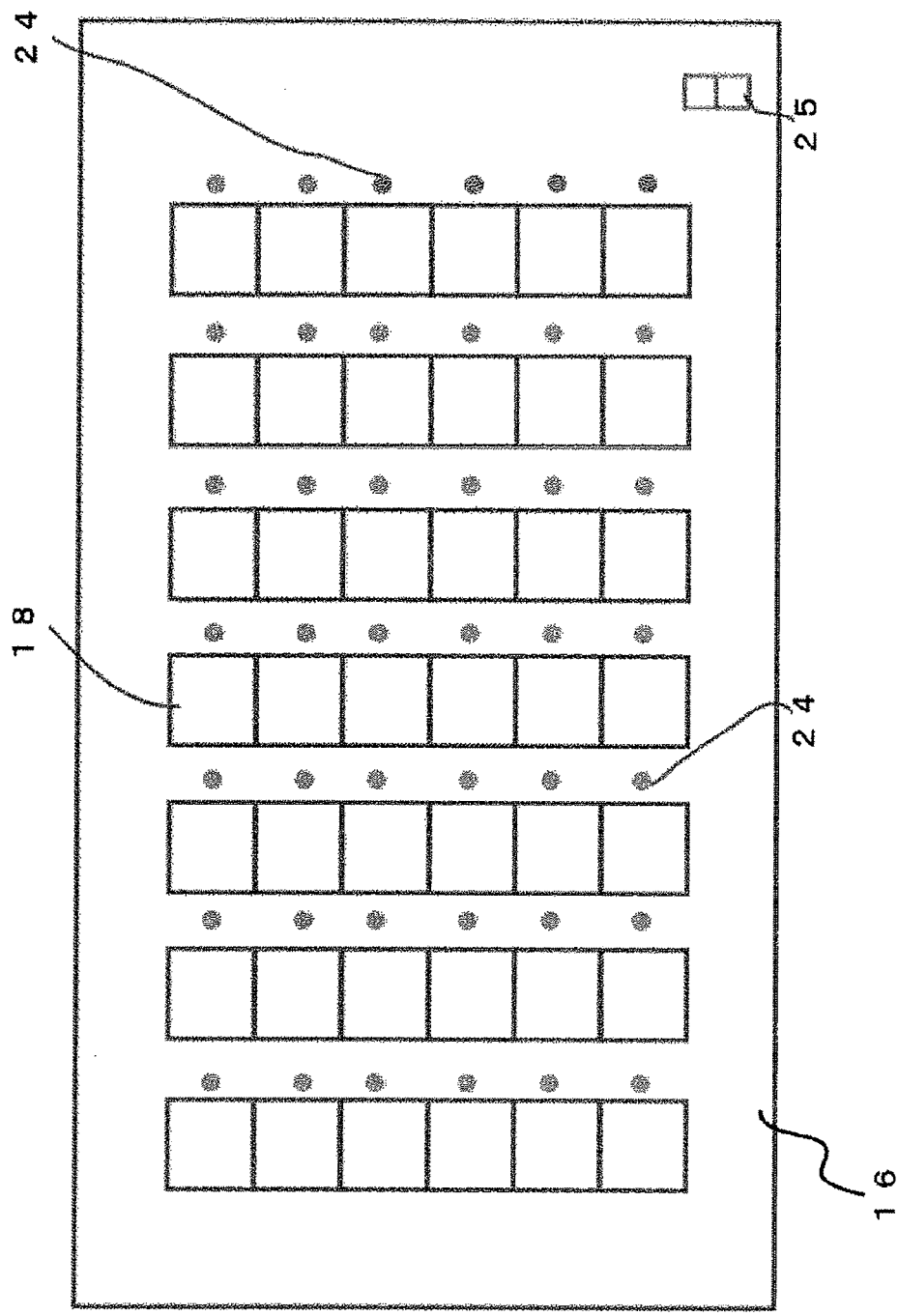
FIG. 6 is a top view schematically showing a medicine manual-distribution supply section according to another embodiment.

That is, as shown in FIG. 6, a position indicating portion 24 such as an LED is provided in a position corresponding to each of the medicine receiving portions 18 (e.g., in the right vicinity of the medicine receiving portion). The position indicating portion indicates which medicine receiving portion 18 must receive the medicine displayed on the prescription details section 13 of the operation panel 6 based on some prescription data. Further, a quantity indicating portion 25 such as a 7-segment display, a liquid crystal display, etc. is provided in one place (if necessary, in several places).

According to the manual medicine supply section 16 having the above-described configuration, the user can identify the medicine receiving portion 18 for receiving the medicine, by confirming the turning-on of the position indicating portion 24. Further, the user can confirm the quantity of the medicine to be placed into the medicine receiving portion 18 from the quantity displayed by the quantity indicating portion 25. The quantity indicating portion 25 is positioned in a position where the user can visually recognize it while confirming the turning-on of the position indicating portion 24. That is, the quantity indicating portion is disposed in the same visual field. Thus, dissimilar to the prior art, the user does not need to shift his eyes to the operation panel. Accordingly, good task efficiency is achieved and the medicine can be placed into the medicine receiving portions 18 without error. Further, the number of expensive quantity indicating portions 25 can be decreased to the minimum necessary extent, thus saving in costs.

Further, the manual medicine supply section 16 may be configured as follows.

That is, as shown in FIG. 8, the position indicating portion 24, which comprises three LEDs that are turned on in different colors (red, blue, yellow), in the vicinity of each of the medicine receiving portions 18. Further, as shown in FIG. 7, when the prescription details section 13 of the operation panel 6 displays a plurality of the medicine names, each medicine is displayed together with the color (in this example, red, blue and yellow circles) that is associated with the corresponding LED of the position indicating portion 24. When some prescription data includes two or three types of medicines, the two or three medicines displayed on the prescription details section 13 are displayed together with the colors that correspond to the colors of the LEDs, respectively.

Further, the manual medicine receiving section 16 turns on the LED associated with the respective color, among the LEDs of the medicine receiving portion 18 that must receive the medicine displayed on the prescription details section 13. As a result, it can be determined instantly which medicine receiving portions 18 must receive which medicine. Thus, the corresponding medicine can be very efficiently placed into the respective medicine receiving portions 18. In this case, the quantity indicating portions 25 may be provided in association with the colors of the position indicating portion 24, respectively. This allows the determination of the quantity of the medicine, which is placed into each medicine receiving portion 18, with regard to each medicine having different color. Thus, the medicine can be more efficiently placed. Further, in this case, the quantity indicating portions 25 may be individually provided in association with each position indicating portion 24 of each of the medicine receiving portions 18, as shown in FIG. 4. Alternatively, the quantity indicating portions may be provided in one place as shown in FIG. 6.

Further, when the prescription data includes four or more types of medicine, three types of medicine may be first displayed on the prescription details section 13. Then, the screen is converted and the remaining medicine may be displayed. Furthermore, as long as four or more types of the medicine remain, the screen may be converted in sequence in order to further display the remaining medicine. Further, the target medicine may be limited to three types and such three types of medicine may be displayed in the prescription details section 13 such that they are distinguishable from others. As a result, even in the case where the prescription data includes four or more types of medicine, they can be handled by means of the LEDs of only three colors. Further, the number of the colors of the LEDs is not limited to three. The LEDs may have two colors or four or more colors. In such a case, the number of the medicine to be displayed on the prescription details section 13 or the number of the distinguishable displays may vary depending upon the number of the LEDs.

In the foregoing embodiment, the display member 20 is provided in the manual medicine receiving section 16, thus guiding the user through a visual sense. The user may be guided through an acoustic sense by using a voice. For example, it is preferred that the message such as " Please put medicine A to the first one by three tablets" and all necessary information such as the medicine name, the receipt place and the received number may be notified to the user by means of a voice. It is a matter of course that such notification includes the received number only, the received number and the medicine name, or the received number and the receipt place. Further, it is preferred that the notification using a voice may be made when an input of the completion of the task is made through the operation panel 6. Further, a sensor (not shown) may be provided in each medicine receiving portion 18. Preferably, the notification using a voice may be made until it is detected through a detection signal from such a sensor that the medicine is received.

DESCRIPTION OF REFERENCE NUMERALS

1 . . . Apparatus body
2 . . . Automatic medicine supply device
3 . . . Manual medicine supply device (medicine supply means)
4 . . . Medicine packaging device
5 . . . Control device (display control means)
6 . . . Operation panel
7 . . . Barcode reader
8 . . . Journal printer
9 . . . Guide screen
10 . . . Title section
11 . . . Pack number section
12 . . . Patient section
13 . . . Prescription details section
14 . . . Others section
15 . . . Slide table
16 . . . Manual medicine supply section
17 . . . Cassette placing section
18 . . . Medicine receiving portion
19 . . . 7-segment display (display portion)
20 . . . Display member (display means)
21 . . . Recess
22 . . . RFID reader
23 . . . Server
24 . . . Position indicating portion
25 . . . Quantity indicating portion

What is claimed is:

1. A medicine supply device, comprising:
a manual medicine supply section having a plurality of medicine receiving portions, the manual medicine supply section being compartmentalized to define the plurality of medicine receiving portions, the medicine receiving portions being configured to receive at least one medicine per a dosing time and discharge the received medicine;
a display including a plurality of display portions and disposed in the manual medicine supply section, the display portions being positioned in adjacent to the medicine receiving portions, respectively, and configured to display a number of a medicine on the corresponding medicine receiving portion in form of a numeral; and
a display controller configured to allow the display portion of the medicine receiving portion, which receives a corresponding medicine among the medicine receiving portions, to operate based on prescription data,
wherein the display controller is configured to allow the display portion to display a number of the medicine, which is received in the medicine receiving portion corresponding to the dosing time of each medicine included in the prescription data, as a numeral, and
wherein a bottom of each medicine receiving portion is configured to be opened to discharge the received medicine.

2. A medicine supply device, comprising:
a manual medicine supply section having a plurality of medicine receiving portions, the manual medicine supply section being compartmentalized to define the plurality of medicine receiving portions, the medicine receiving portions being configured to randomly receive at least one medicine and discharge the received medicine;
a display disposed in the manual medicine supply section and including:
a plurality of first display portions, the first display portions being positioned adjacent to the medicine receiving portions, respectively; and
a second display portion provided in the manual medicine supply section and configured to display a number of a medicine on the corresponding medicine receiving portion in form of a numeral; and
a display controller configured to allow the first display portion of the medicine receiving portion among the medicine receiving portions, in which a corresponding medicine is received, and the second display portion to operate based on prescription data,
wherein the display controller is configured to allow the second display portion to display the number of the medicine of the medicine receiving portion, in which the corresponding medicine is received, as a numeral, and
wherein a bottom of each medicine receiving portion is configured to be opened to discharge the received medicine.

* * * * *